United States Patent [19]

Hammond et al.

[11] 4,253,980
[45] Mar. 3, 1981

[54] QUATERNARY AMMONIUM SALT OF ESTER-LACTONE AND HYDROCARBON OIL CONTAINING SAME

[75] Inventors: Kenneth G. Hammond; Harry Chafetz, both of Poughkeepsie, N.Y.

[73] Assignee: Texaco Inc., White Plains, N.Y.

[21] Appl. No.: 53,011

[22] Filed: Jun. 28, 1979

[51] Int. Cl.³ ............... C07D 405/12; C10M 5/20
[52] U.S. Cl. ............................ 252/34; 546/268; 546/283; 546/342
[58] Field of Search ............ 252/34; 546/342, 283, 546/268

[56] References Cited

U.S. PATENT DOCUMENTS

| 3,522,179 | 7/1970 | LeSuer | 252/51.5 A |
| 3,778,371 | 12/1973 | Malec | 252/34 |
| 3,936,472 | 2/1976 | Kinney et al. | 260/343.6 |

Primary Examiner—Alan L. Rotman
Attorney, Agent, or Firm—Carl G. Ries; Robert A. Kulason; James J. O'Loughlin

[57] ABSTRACT

A quaternary ammonium salt of an ester-lacetone represented by the formula

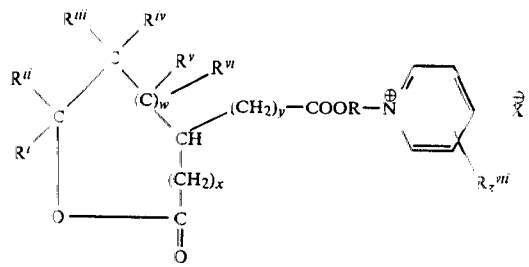

in which w represents 0 or 1, x and y alternately represent 0 and 1, z has value from 0 to 4, $R^i$, $R^{ii}$, $R^{iii}$ and $R^{iv}$, in instances where w is equal to 0, represent hydrogen or akyl radicals at least one of which is a hydrocarbyl radical having from 50–200 carbon atoms; in instances where w is equal to 1 at least one of $R^i$, $R^{ii}$, $R^{iii}$, $R^{iv}$, $R^v$ or $R^{vi}$, represents a hydrocarbyl radical of 50–200 carbon atoms and the remaining substituents are hydrogen or lower alkyl radicals, R is a divalent radical having from 2–10 carbon, or carbon and oxygen atoms, $R^{vii}$ is hydrogen or a hydrocarbyl radical, and X is an anion is provided, as well as a method of preparation and a hydrocarbon lubricating oil composition containing same.

28 Claims, No Drawings

QUATERNARY AMMONIUM SALT OF ESTER-LACTONE AND HYDROCARBON OIL CONTAINING SAME

BACKGROUND OF THE INVENTION

1. Field of the Invention

Internal combustion engines operate under a wide range of temperatures including low-temperature stop-and-go service as well as high temperature conditions produced by continuous high speed driving. Stop-and-go driving, particularly during cold, damp weather conditions, leads to the formation of a sludge in the crankcase and oil passages of a gasoline engine. This sludge seriously limits the ability of the crankcase oil to lubricate the engine. In addition, the sludge tends to contribute to rust formation within the engine. The noted problems are compounded by lubrication service maintenance recommendations calling for extended oil drain intervals.

It is known to employ nitrogen-containing dispersants and/or detergents in the formulation of crankcase lubricating oil compositions. Many of the known dispersant/detergent compounds are based on the reaction of an alkenylsuccinic acid or anhydride with an amine or polyamine to produce an alkenylsuccinimide or an alkenylsuccinamic acid as determined by selected conditions of reaction.

It is also known to chlorinate alkenylsuccinic acid or anhydride prior to the reaction with an amine or polyamine in order to produce a reaction product in which a portion of the amine or polyamine is attached directly to the alkenyl radical of the alkenylsuccinic acid or anhydride. The thrust of many of these processes is to produce a dispersant having a relatively high level of nitrogen. The noted known processes generally result in the production of a dispersant reaction product typically containing from about 0.5 to 5% nitrogen. These dispersant additives exhibited a high degree of oil solubility and have been found to be effective for dispersing the sludge that is formed under severe low temperature stop-and-go engine operating conditions. However, it has become increasingly difficult to formulate lubricants with these additives which meet the present requirements with respect to the prevention or inhibition of the formation of varnish.

2. Description of the Prior Art

U.S. Pat. No. 3,155,685 discloses a step-wise method for preparing an ester lactone by reacting a 2-alkenyl-succinic anhydride in which the alkenyl radical has less than 32 carbon atoms with a monohydric alcohol to form a monoester-acid intermediate product, and further reacting this intermediate product in the presence of an acid catalyst to produce an ester lactone useful as a plasticizer.

U.S. Pat. No. 3,522,179 discloses esters of hydrocarbon-substituted succinic acid which are prepared by reacting a chlorinated polyolefin with maleic anhydride to form an intermediate hydrocarbon-substituted succinic anhydride and then reacting the intermediate with a glycol, such as neopentyl glycol, or polyethylene glycol to form an acid ester.

U.S. Pat. No. 3,778,371 discloses lubricant and fuel compositions containing N-hydrocarbyl-substituted quaternary ammonium salts prepared by reacting a high molecular weight aliphatic hydrocarbon halide with a tertiary amine.

U.S. Pat. No. 3,936,472 discloses a method for preparing alkyl lactone esters by reacting an alkenylsuccinic anhydride with an alcohol or thiol in the presence of an acid-reacting catalyst and optionally further reacting the alkyl lactone ester with an amine.

SUMMARY OF THE INVENTION

The quaternary ammonium salt of an ester-lactone of this invention is represented by the formula:

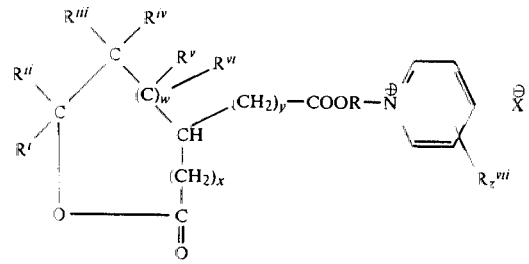

in which w represents 0 or 1, x and y alternately represent 0 and 1, z has value from 0 to 4, $R^i$, $R^{ii}$, $R^{iii}$ and $R^{iv}$, in instances where w is equal to 0, represent hydrogen or alkyl radicals at least one of which is a hydrocarbyl radical having from 50–200 carbon atoms; in instances where w is equal to 1 at least one of $R^i$, $R^{ii}$, $R^{iii}$, $R^{iv}$, $R^v$ or $R^{vi}$, represents a hydrocarbyl radical of 50–200 carbon atoms and the remaining substituents are hydrogen or lower alkyl radicals, R is a divalent radical having from 2–10 carbon, or carbon and oxygen atoms, $R^{vii}$ is hydrogen or a hydrocarbyl radical, and X is an anion selected from the group consisting of halides, sulfates, carbonates, sulfides, borates, carboxylates, and phosphates.

The novel quaternary salt is prepared by reacting an alkenyl-succinic anhydride with a haloalcohol, employing a mole ratio of one mole of an alkenylsuccinic anhydride with from 1 to 1.5 moles of a halogenated monohydric alcohol in the presence of an acid-reacting catalyst followed by a reaction with a heterocyclic tertiary amine to produce the prescribed quaternary ammonium salt.

The dispersant detergent lubricating oil composition of the invention comprises a lubricating oil base and an effective amount of the prescribed quaternary ammonium salt.

DESCRIPTION OF THE PREFERRED EMBODIMENTS

The novel quaternary ammonium salt of an ester-lactone of this invention is represented by the formula:

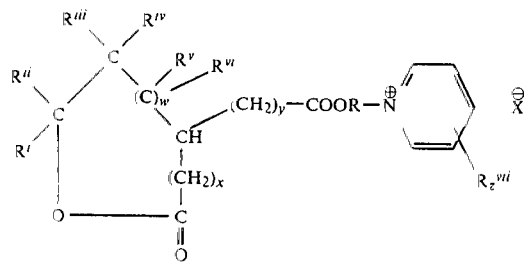

in which w represents 0 or 1, x and y alternately represent 0 and 1, z has value from 0 to 4, $R^i$, $R^{ii}$, $R^{iii}$ and $R^{iv}$, in instances where w is equal to 0, represent hydrogen or alkyl radicals at least one of which is a hydrocarbyl radical having from 50–200 carbon atoms; in instances where w is equal to 1 at least one of $R^i$, $R^{ii}$, $R^{iii}$, $R^{iv}$, $R^v$ or $R^{vi}$, represents a hydrocarbyl radical of 50–200 carbon atoms and the remaining substituents are hydrogen or lower alkyl radicals, R is a divalent radical having from 2–10 carbon, or carbon and oxygen atoms, $R^{vii}$ is hydrogen or a hydrocarbyl radical, and X is an anion selected from the group consisting of halides, sulfates, carbonates, sulfites, borates, carboxylates and phosphates.

In the above formula, the divalent radical represented by R can be an aliphatic hydrocarbon radical or it can be an ether or a polyether radical represented by the formulas:

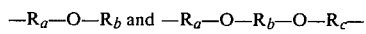

wherein $R_a$, $R_b$ and $R_c$ are aliphatic hydrocarbon radicals having from 2 to 4 carbon atoms each.

The hydrocarbon radical represented by $R^{vii}$ in the above formula can be an aliphatic hydrocarbon radical or an aromatic radical, or one or two pairs of $R^{vii}$ can be interconnected to form one or two fused aromatic rings respectively with the principal heterocyclic aromatic ring.

When X is a halogen atom it is preferably a chloride or a bromide ion.

A preferred quaternary ammonium salt of an ester-lactone is the salt of an ester-gamma-lactone represented by the formula:

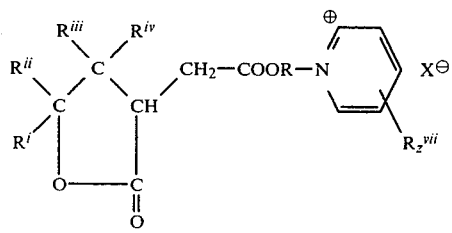

in which $R^i$ or $R^{iii}$ represents a hydrocarbyl radical having from 50 to 200 carbon atoms, the other substituent, $R^{ii}$, and $R^{iv}$ represent hydrogen or methyl radicals, R is a divalent hydrocarbon radical having from 2 to 6 carbon atoms, X is an anion selected from the group consisting of chloride, bromide, sulfate and borate ions, $R^{vii}$ is hydrogen or an aliphatic hydrocarbon radical having from 1 to 3 carbon atoms and z has a value from 0 to 2.

A particularly preferred quaternary ammonium salt of an ester-gamma-lactone is one in which $R^i$ or $R^{iii}$ is a monovalent hydrocarbon radical having from 75 to 150 carbon atoms and R has from 2 to 4 carbon atoms.

Another preferred quaternary ammonium salt of an ester-lactone of this invention is an ester-delta-lactone represented by the formula:

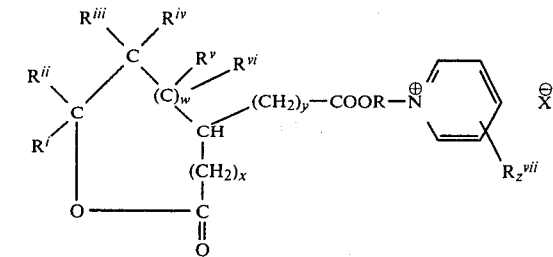

in which w, x, and y represent 0, 1, 0, or 1, 0, 1 respectively, $R^i$, $R^{ii}$, $R^{iii}$ and $R^{iv}$, in the case where w equals 0, represents hydrogen or alkyl radicals at least one of which has from 50–200 carbon atoms, $R^i$, $R^{ii}$, $R^{iii}$, $R^{iv}$, $R^v$ or $R^{vi}$, in the case where w equals 1 represents a hydrocarbyl radical of 50–200 carbon atoms and the remaining are hydrogen or lower alkyl radicals, and X and z has the value set forth herein above under the description of the preferred ester-gamma-lactone quaternary ammonium salt.

Another preferred quaternary ammonium salt of an ester-lactone of this invention is an ester-epsilon-lactone represented by the formula:

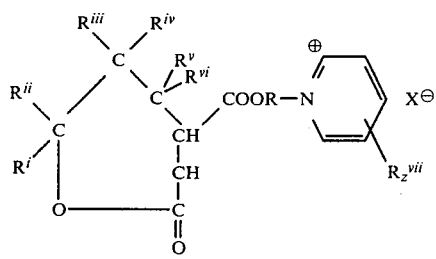

in which $R^i$, $R^{ii}$, $R^{iii}$, $R^{iv}$, $R^v$ and $R^{vi}$ represent hydrogen or alkyl radicals at least one of which has between 50 and 200 carbon atoms and $R^{vii}$, X and z have the values set forth hereinabove under the description of the preferred ester-gamma lactone quaternary ammonium salt.

The prescribed quaternary ammonium salt of the ester-lactone of the invention is prepared in a two-step reaction. In general, an alkenyl succinic anhydride is reacted with a halogenated alcohol in the presence of an acid-reacting catalyst to produce the intermediate ester-lactone. This, in turn, is reacted with a heterocyclic tertiary amine to produce the quaternary ammonium salt of the ester-lactone.

The preparation of alkenylsuccinic acid anhydrides is well known to those skilled in the art. Alkenylsuccinic acid anhydride can be prepared by heating a polyolefin of suitable molecular weight with maleic anhydride to produce an alkenylsuccinic acid anhydride. The polyolefin employed is one obtained from the polymerization of a $C_2$ to $C_6$ monoolefin or a mixture of monoolefins under conventional polymerization conditions. For the purposes of this invention, the polymer produced will be an unsaturated polymer having a molecular weight corresponding to the desired molecular weight of the alkenyl radical in the prescribed quaternary ammonium salt, i.e., a molecular weight from about 700 to 2800 as determined by vapor pressure osmometry. This reaction is described in the following U.S. Pat. Nos., namely, 3,024,195, 3,288,714, and 3,476,774, the disclosures of which are incorporated herein by reference.

The alkenylsuccinic anhydride reactant is represented by the formula:

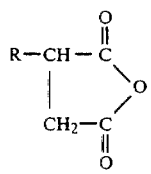

in which R is an unsaturated hydrocarbon or alkenyl radical having from about 50 to 200 carbon atoms.

Examples of specific alkenyl-substituted succinic acid anhydrides which can be employed for preparing the prescribed quaternary ammonium salts of this invention include the following: polybutenyl-, polypropenyl- and polypentenyl- succinic acid anhydrides.

The haloalkanol, which can be employed for preparing the prescribed quaternary ammonium salt, is represented by the formula X—R—OH in which X is a halogen atom and R is a divalent radical having from 2 to 10 carbons, or carbon and oxygen atoms. The halogen atom can be a chloride, bromide or an iodide atom, with the chloride atom being preferred. Typical examples of suitable haloalkanol compounds include 2-chloroethanol, 2-bromoethanol, 3-chloropropanol, 3-bromopropanol, 4-chlorobutanol, 4-bromobutanol, 4-iodobutanol, 5-chloropentanol, 5-bromopentanol, 6-chlorohexanol, 6-bromohexanol, and 2-(2-chloroethoxy)-ethanol.

The mole ratio of haloalkanol to alkenylsuccinic anhydride required to prepare the intermediate product necessary in the reaction leading to the prescribed quaternary ammonium salt of an ester lactone is from 1 to 1.5 moles of haloalkanol to 1 mole of alkenylsuccinic anhydride with the preferred ratio being from 1.2 to 1.5 moles of the haloalkanol to a mole of alkenylsuccinic anhydride. Higher mole ratios of the haloakanol either have no significant effect on the amount of the intermediate product produced or substantially reduce the amount of the essential ester-lactone intermediate produced for reasons that are not completely understood.

The reaction of an alkenylsuccinic anhydride with a haloalkanol to form the ester-lactone precursor of the prescribed quaternary ammonium salt must be conducted either concurrently or sequentially in the presence of an acid-reacting catalyst. This catalyst is essential for effecting the lactone ring formation and also serves to promote the esterification reaction. Suitable acid-reacting catalysts include sulfuric acid, phosphoric acid, polyphosphoric acid, sulfonic acid, p-toluene sulfonic acid, phosphonic acid, hydrogen chloride, hydrogen bromide, sulfonated cation exchange resins and crystalline alumino-silicate in the acid form.

The amount of the acid-reacting catalyst used is not critical. In general, from about 0.2 to 5.0 weight percent of the acid-catalyst based on the amount of the alkenylsuccinic acid anhydride will promote the ester-lactone reaction.

This reaction can be conducted over a broad range of temperatures. Useful temperatures range from about 20° to 150° C. with the preferred reaction temperature being from about 80° to 120° C.

The intermediate ester-lactone product produced in the first step of this process leading to the prescribed quaternary ammonium salt is represented by the formula:

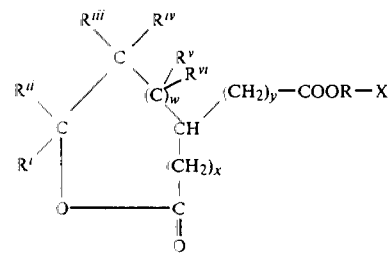

in which R, $R^i$, $R^{ii}$, $R^{iii}$, $R^{iv}$, $R^v$, $R^{vi}$, w, x, y, and X have the same values noted above for the finished salt.

The intermediate ester-lactone product is reacted with a tertiary heteroaromatic amine in order to form the prescribed quaternary ammonium salt. The effective tertiary heteroaromatic amine is represented by the formula:

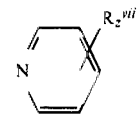

in which z is a number from 0 to 4 and $R^{vii}$ is hydrogen, or a hydrocarbyl radical having from 1 to 8 carbon atoms, or one or two pairs of "R"s are interconnected to form one or two fused aromatic rings respectively.

The preferred heteroaromatic amine is one in which $R^{vii}$ is hydrogen or a lower aliphatic hydrocarbon radical having from 1 to 4 carbon atoms.

Examples of suitable tertiary heteroaromatic amines include pyridine, 2-methylpyridine, 2,3-dimethylpyridine, 4-methylpyridine, quinoline, isoquinoline and phenazine.

The following procedures, Procedures A through C, describe the methods that were employed for preparing the ester-lactone intermediate used in the preparation of the prescribed quaternary ammonium salt compounds of this invention.

Procedure A

A polyisobutenyl (about 1300 molecular weight or about 93 carbon atoms) succinic anhydride, the haloalcohol and the acid catalyst are charged to an appropriate sized flask equipped with a reflux condenser, stirrer and thermometer. The mixture is heated at the specified temperature for the indicated time period. The reflux condenser is removed and a distillation head is installed after which the mixture is further heated at 120°-130° C. under reduced pressure in order to remove small amounts of volatile materials (primarily unreacted alcohol) and to complete formation of the product. The product is then subjected to infrared analysis. Gamma-lactone formation is indicated by absorption at the 1770 $cm^{-1}$ wavelength, and carboxylate ester and delta- and epsilon-lactone formation at the 1745 $cm^{-1}$.

Procedure C

A polyisobutenyl (about 1300 molecular weight or about 93 carbon atoms) succinic anhydride, the haloalcohol and the acid catalyst are charged to a suitable reaction vessel. The mixture is heated at the specified temperature for the indicated time period and then diluted with a light hydrocarbon solvent, heptane or isooctane. The resulting solution is slurried with sodium carbonate (about 3.5 equivalents per equivalent of acid), filtered, and then stripped of volatile materials. The product is then subjected to infrared analysis as in Procedure A above.

Procedure B

A polybutenyl (about 1300 molecular weight or about 93 carbon atoms) succinic anhydride and the haloalcohol are charged to a reaction vessel as above. The mixture is heated at 80°–85° C. for one-half hour in order to form an intermediate monosuccinate (IR analysis: carboxylate ester 1745 cm$^{-1}$, carboxylic acid 1710 cm$^{-1}$). The mineral acid catalyst is added and the mixture heated at 80°–85° C. for an additional half hour and then at 120° C. under reduced pressure in order to remove a small amount of volatile material (primarily unreacted alcohol) and to complete product formation.

The following Table gives the details of preparation and the results obtained in Examples 1 through 15 for the ester-lactone intermediate product.

Procedure E

The reaction product obtained according to Procedure E (100 parts) is diluted with a light hydrocarbon (heptane or isooctane, 200 parts) and the resulting solution was extracted with methanol (100 parts). The methanol layer is allowed to separate and was then removed from the vessel and discarded. The remaining light hydrocarbon solution was stripped at 90°–100° C. under a 1–25 mm Hg vacuum to yield an oil concentrate of the product.

The appearance of the finished additive can often be beneficially modified by conducting the ester-lactone/amine reaction in the presence of base, for example sodium carbonate, to neutralize amine hydrochloride and/or boric acid to minimize color body formation.

Procedure F

The ester-lactone, the tertiary amine and the other

TABLE I
INTERMEDIATE ESTER-LACTONE

| | REACTANTS | | | | | ANALYSIS OF PRODUCT | | | |
|---|---|---|---|---|---|---|---|---|---|
| Example | Moles of Polisobutenyl (1300 m.w.) Succinic Anhydride[1] | Moles of Haloalkanol[2] | Moles of Sulfuric Acid[3] | Procedure | Mole Ratio Anh./Alc/Acid | Reaction Conditions Temp. °C. | Time Hr. | % Chlorine | Moles of Alcohol per Moles of Anhydride Employed |
| 1 | 0.10 | 0.50 | 0.01 | A | 1.0–5.0–0.1 | 80 | 5.0 | 2.4 | 1.5 |
| 2 | 0.20 | 0.43 | 0.02 | A | 1.0–2.1–0.1 | 80 | 6.0 | 2.2 | 1.4 |
| 3 | 1.00 | 1.5 | 0.10 | A | 1.0–1.5–0.1 | 80 | 1.0 | 2.0 | 1.3 |
| 4 | 0.20 | 0.30 | 0.02 | A | 1.0–1.5–0.1 | 80 | 1.0 | 1.9 | 1.2 |
| 5 | 1.00 | 1.43 | 0.10 | A | 1.0–1.4–0.1 | 80 | 0.5 | 2.0 | 1.3 |
| 6 | 23.4 | 32.8 | 2.30 | A | 1.0–1.4–0.1 | 80 | 0.5 | 2.3 | 1.3 |
| 7 | 1.0 | 1.41 | 0.10 | A | 1.0–1.4–0.1 | 80 | 0.5 | 2.0 | 1.3 |
| 8 | 0.80 | 1.07 | 0.08 | A | 1.0–1.3–0.1 | 80 | 0.5 | 2.1 | 1.2 |
| 9 | 0.82 | 1.09 | 0.08 | B | 1.0–1.3–0.1 | 80 | 0.5 | 2.1 | 1.2 |
| 10 | 0.69 | 4.40 | 0.034 | C | 1.0–6.4–0.05 | 82 | 7.0 | 2.4 | 1.5 |
| 11 | 0.20 | 0.40 | 0.02 | A | 1.0–2.0–0.1 | 80 | 2.0 | 1.7 | 1.0 |
| 12 | 0.50 | 0.75 | 0.05 | A | 1.0–1.5–0.1 | 80 | 1.0 | 1.6 | 1.0 |
| 13 | 0.21 | 2.1 | 0.038 | C | 1.0–10.0–0.2 | 115 | 6.0 | 2.5 | 1.3 |
| 14 | 0.38 | 1.5 | 0.036 | C | 1.0–3.8–0.1 | 115 | 18.0 | 2.5 | 1.4 |
| 15 | 0.17 | 1.0 | 0.008 | C | 1.0–5.1–0.05 | 80 | 6.0 | 1.9 | 1.2 |

[1]The saponification number was 53 for Examples 1–5, 9, 11, 12 and 15; 58 for Examples 6–8 and 10; 64 for Example 13 and 61 for Example 14; all of these reactants contained some unreacted polyisobutene.
[2]4-chlorobutanol was used in Examples 1–10, 2-chloroethanol in Examples 11–14, and 2-(2-chloroethoxy)-ethanol in Example 15.
[3]Methyl sulfonic acid was used in Example 4.

EXAMPLES 16–26

The quaternary ammonium salts of this invention were prepared by one of the following procedures.

Procedure D

The ester-lactone and the tertiary amine are charged to an appropriately sized flask equipped with a reflux condenser, stirrer, nitrogen inlet tube, and thermometer. The mixture is stirred and heated under a nitrogen atmosphere at the specified temperature for the indicated time period. The mixture is diluted with a light hydrocarbon, (heptane or isooctane) and some mineral oil, filtered through diatomaceous earth, and then stripped at 90°–110° C. under a vacuum of from 1–25 mm of mercury to remove the light hydrocarbon and the unreacted amine and yield an oil concentrate of the product.

reagent (if used) are charged to a reactor vessel and stirred under a nitrogen atmosphere at the specified temperature for the indicated period of time. The mixture is diluted with oil and the resulting solution stripped at 90°–150° C. under a 0.1–25 mm Hg vacuum to remove unreacted amine. After stripping, the mixture is filtered through diatomaceous earth to yield an oil concentrate of the product.

Procedure G

The reaction product obtained according to Procedure F (100 parts) is diluted with heptane or isooctane (200 parts) and extracted with methanol (100 parts). The methanol layer is allowed to separate and is then removed from the vessel and discharged. The remaining light hydrocarbon solution is stripped at 90°–100° C. under a vacuum of 1–25 mm Hg to yield an oil concentrate of the product.

The reactants, reaction parameters and product analyses for Examples 16 through 26 are summarized in Table II below:

TABLE II

| Ex. No. | Ester-Lactone Ex. No. in Table I | Tertiary Amine Gr | Tertiary Amine Identity | Gr | Mole Ratio Amine/ Chloride in Ester-Lactone | Prep. Procedure[1] | Reaction Conditions Temp. (°C.) | Reaction Conditions Time (Hr) | % Diluent Oil in Product | Product Analyses % Cl | Product Analyses % N |
|---|---|---|---|---|---|---|---|---|---|---|---|
| 16 | 2 | 200 | 4-Picoline | 114 | 10.1 | D | 130 | 8.0 | 50 | 1.15 | 0.60 |
| 17 | 2 | 200 | 4-Picoline | 114 | 10.1 | E | 130 | 8.0 | 56 | 0.69 | 0.19 |
| 18 | 3 | 800 | 4-Picoline | 200 | 4.7 | D | 130 | 8.0 | 50 | 0.95 | 0.37 |
| 19 | 6 | 42,900 | 4-Picoline | 13,000 | 5.0 | F | 130 | 6.0 | 50 | 1.04 | 0.45 |
| 20 | 6 | 42,900 | 4-Picoline | 13,000 | 5.0 | G | 130 | 6.0 | 53 | 0.75 | 0.27 |
| 21 | 6 | 500 | 4-Picoline | 239 | 7.9 | F | 130 | 7.0 | 50 | 0.69 | 0.30 |
| 22 | 6 | 500 | 4-Picoline | 239 | 7.9 | F | 130 | 7.0 | 50 | 0.87 | 0.29 |
| 23 | 6 | 210 | Isoquinoline | 84 | 4.7 | F | 130 | 8.0 | 50 | 1.01 | 0.72 |
| 24 | 8 | 1000 | 4-Picoline | 870 | 13.8 | E | 135 | 8.0 | 57 | 1.03 | 0.39 |
| 25 | 14 | 125 | 4-Picoline | 120 | 14.5 | D | 135 | 8.0 | 0 | 2.20 | 0.99 |
| 26 | 15 | 156 | 4-Picoline | 69 | 8.9 | D | 125 | 8.0 | 0 | 1.77 | 1.18 |

[1] Boric acid (40 Gr) was used in Ex. No. 21, and sodium carbonate (40 Gr) was used in Ex. No. 22.

The performance and/or appearance of the additive can often be beneficially modified by exchanging the halide anion in the compound with another anion, such as a borate, sulfate, phosphate, phosphonate, sulfite or sulfonate, disclosed above. In general, the original quaternary ammonium salt is mixed with an acidic compound having the desired anion prescribed hereinabove and reacted therewith at a moderately elevated temperature ranging from about 80° to 120° C. while removing the displaced hydrogen halide under reduced pressure. The resulting modified salt is significantly improved as a lubricating oil additive.

EXAMPLE 27

A portion of the product of Example 19 (1120 gr) and 112 gr of boric acid were combined and stirred under a nitrogen purge at 100° C. for 4 hours. The mixture was filtered while hot through diatomaceous earth to yield a product which contained 0.92% Cl, 0.34% N and 0.25% B.

EXAMPLE 28

A portion of the product of Example 19 (2009 gr) and 200 gr of boric acid were combined and stirred at 100° C. under reduced pressure (about 1 mm) for 4 hours in order to remove hydrogen chloride. The mixture was filtered while hot to yield a product which contained 0.44% Cl, 0.35% N, and 0.63% B.

EXAMPLE 29

A portion of the product of Example 19 (250 gr), 7.1 gr of concentrated sulfuric acid, 250 ml of isooctane and 125 ml of methanol were combined and shaken until homogenous. A methanol solution which separated from the mixture was removed from the vessel and discarded. The remaining isooctane solution was stripped at 95° C. (18 mm) to yield an oil concentrate which contained 0.33% Cl, 0.24% N and 0.42% S.

EXAMPLE 30

A portion of the product of Example 19 (300 gr) and 8.3 gr of concentrated sulfuric acid were combined and stirred at 100° C. under reduced pressure (about 1 mm) in order to remove hydrogen chloride. The mixture was filtered while hot through diatomaceous earth to yield a product which contained 0.4% Cl, 0.42% N, and 0.78% S.

The lubricant composition of the invention comprises a major amount of a mineral, hydrocarbon oil or synthetic oil of lubricating viscosity and an effective detergent-dispersant amount of the prescribed quaternary ammonium salt of an ester lactone. Advantageously, in the finished lubricating oil composition, the prescribed quaternary ammonium salt content ranges between about 0.1 and 10 percent by weight, preferably between about 0.5 and 5 weight percent. In the lubricating oil concentrates, from which the finished lubricating compositions are derived via the addition of added lubricating oil, quaternary ammonium salt contents between about 10 and 50 weight percent are found.

The hydrocarbon oil in the finished lubricating composition advantageously constitutes at least about 85 weight percent and preferably between about 90 and 98 weight percent of the composition, and in the lube oil concentrates between about 50 and 90 weight percent of the composition. It is to be noted that even in the lubricating oil concentrates the prescribed quarternary ammonium salt will exhibit detergent-dispersancy as well as varnish inhibition.

Examples of the hydrocarbon base oils contemplated herein are the naphthenic base, paraffinic base and mixed base mineral oils, lubricating oils derived from coal products and synthetic oils, e.g., alkylene polymers such as polypropylene and polyisobutylene of a molecular weight of between about 250 and 2500. Advantageously, a lubricating base oil having a lubricating oil viscosity at 100° F. of between about 50 and 1000, preferably between about 100 and 600, are normally employed for the lubricant compositions and concentrates thereof. (SUS basis)

In the contemplated finished lubricating oil compositions other additives may be included in addition to the dispersant of the invention. The additives may be any of the suitable standard pour depressants, viscosity index improvers, oxidation and corrosion inhibitors, antifoamants, supplementary detergent-dispersants, etc. The choice of the particular additional additives to be included in the finished oils and the particular amounts thereof will depend on the use and conditions desired for the finished oil product.

Specific examples of the supplementary additives are as follows:

A widely used and suitable VI improver is the polymethacrylate having the general formula:

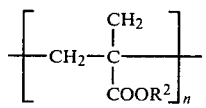

where $R^2$ is an aliphatic radical of from 1 to 20 carbons and n is an integer of between about 600 and 35,000. One of the most suitable VI improvers is the tetrapolymer of butyl methacrylate, dodecyl methacrylate, octadecyl methacrylate, and dimethylaminoethyl methacrylate having a respective component weight ratio in the polymer of about 4:10.5:1. Another VI improver is a copolymer of ethylene and propylene having a molecular weight of 20,000 to 50,000 containing 30 to 40 percent propylene in the copolymer in admixture with solvent neutral oil (100 E Pale Oil) comprising 13 weight percent copolymer and 87 weight percent oil. The VI improvers are normally employed in the finished lubricant compositions in quantities between about 0.1 and 10 percent by weight.

One of the commonly employed lube oil corrosion inhibitors and antioxidants are the divalent dialkyl dithiophosphates resulting from the neutralization of a $P_2S_5$-alcohol reaction product with a divalent metal or divalent metal oxide. Barium and zinc dialkyl dithiophosphate are specific examples. Another class of antioxidants are the polyalkylated diphenylamines, such as a mixture of 2,2'-diethyl-4,4'-dioctylphenylamine and 2,2'-diethyl-4-p-octyldiphenylamine. The corrosion and oxidation inhibitors are usually present in the finished lubricating oil compositions in concentrations of between about 0.1 and 3 weight percent.

Examples of supplementary detergent-dispersants which can be employed are the monoethoxylated inorganic phosphorus acid-free, steam hydrolyzed polyalkylene (500–50,000 m.w.)-$P_2S_5$ reaction product, alkaline earth metal alkylphenolates, such as barium nonylphenolate, barium dodecylcresolate, calcium dodecylphenolate and the calcium carbonate overbased calcium alkaryl sulfonates formed by blowing a mixture of calcium hydroxide and calcium alkaryl sulfonate, e.g., calcium alkylbenzene sulfonate of about 900 m.w. with carbon dioxide to form a product having a total base number (TBN) of 50 or more, e.g., 300 to 400.

If antifoamants are employed in the finished compositions, one widely used class which is suitable are the dimethyl silicone polymers employed in amounts of between about 10 and 1000 ppm.

The following tests were employed to determine the dispersancy and varnish inhibiting effect of the lubricant composition of the invention:

BENCH VC TEST

In the Bench VC Test, a mixture containing the test oil and a diluent are heated at an elevated temperature. After heating, the turbidity of the resultant mixture is measured. A low % turbidity (0–10) is indicative of good dispersancy while high results (20–100) are indicative of oils of increasingly poor dispersancy.

FORD SEQUENCE VC TEST

This test is the Ford Sequence VC Test and is detailed in "Multicylinder Test Sequence for Evaluating Automotive Engine OIls" ASTM Special Technical Publication under 315-E. This procedure is used to evaluate crankcase motor oils with respect to sludge and varnish deposits as well as their ability to keep the positive crankcase ventilation (PCV) valve clean and functioning properly. Ratings of 0 to 10 are given, 10 representing absolutely clean and 0 rating representing heavy sludge and varnish deposits and a clogged PCV valve. SE performance criteria for the test specify a ≧8.5 for average sludge, ≧ 8.0 for average varnish and ≧7.9 for piston skirt varnish.

EXAMPLE 31

A fully formulated SAE Grade 10W-40 lubricating oil composition containing the quaternary ammonium salt of an ester-lactone of the invention was tested for its dispersing effectiveness in the Bench VC Test in comparison to a fully formulated base oil without the amine salt dispersant, and to fully formulated lubricating oil compositions containing either a commercial succinimide dispersant or the intermediate ester-lactone.

The base blend employed contained the following conventional additives:
- 0.15 weight % zinc as zinc dialkyldithiophosphate
- 0.23 weight % calcium as overbased calcium sulfonate
- 0.25 weight % alkylated diphenylamine antioxidant
- 11.5 weight % ethylene-propylene copolymer VI improver
- 0.15 weight % ethoxylated alkylphenol
- 0.10 weight % methacrylate pour depressant
- 150 ppm silicone anitfoamant
- mineral oil—balance The quaternary ammonium salt dispersant of the invention was added to the base blend at two concentrations on an oil-free basis and then tested in the Bench VC Test.

The results are set forth in the table below:

TABLE III

| | BENCH VC TEST | |
|---|---|---|
| Run | Wt. % of Additive in Base Blend | Turbidity |
| 1 | Base Blend (no dispersant) | 97.5 |
| 2 | Example 16 - 4.0 | 3.0 |
| 3 | Example 16 - 3.0 | 3.0 |
| 4 | Example 17 - 4.0 | 1.5 |
| 5 | Example 17 - 3.0 | 4.0 |
| 6 | Example 18 - 4.0 | 2.0 |
| 7 | Example 18 - 3.0 | 4.0 |
| 8 | Example 19 - 4.0 | 3.0 |
| 9 | Example 19 - 3.0 | 5.5 |
| 10 | Example 20 - 4.0 | 3.0 |
| 11 | Example 20 - 3.0 | 4.0 |
| 12 | Example 21 - 4.0 | 4.0 |
| 13 | Example 21 - 3.0 | 6.0 |
| 14 | Example 22 - 4.0 | 2.0 |
| 15 | Example 22 - 3.0 | 3.5 |
| 16 | Example 23 - 4.0 | 1.0 |
| 17 | Example 23 - 3.0 | 13.0 |
| 18 | Example 24 - 4.0 | 4.0 |
| 19 | Example 24 - 3.0 | 4.5 |
| 20 | Example 25 - 4.0 | 6.5 |
| 21 | Example 26 - 4.0 | 3.0 |
| 22 | Example 26 - 3.0 | 12.0 |
| 23 | Example 27 - 4.0 | 3.0 |
| 24 | Example 27 - 3.0 | 7.0 |
| 25 | Example 28 - 4.0 | 4.0 |
| 26 | Example 28 - 3.0 | 8.5 |
| 27 | Example 29 - 4.0 | 1.5 |
| 28 | Example 29 - 3.0 | 6.5 |
| 29 | Example 30 - 4.0 | 5.0 |
| 30 | Succinimide Dispersant - 4.0 | 4.0 |
| 31 | Succinimide Dispersant - 3.0 | 9.5 |
| 32 | Ester-Lactone Example 6 - 4.0 | 97.5 |
| 33 | Ester-Lactone Example 6 - 3.0 | 96.5 |

The foregoing tests demonstrate that the prescribed quaternary amine salts of an ester-lactone are excellent dispersants for a lubricating oil composition and exhibit superior effectiveness in comparison to a commercial succinimide dispersant.

EXAMPLE 32

This example illustrates the dispersant properties of the lubricating oil compositions of the invention in the Ford Sequence VC Test described above. The base blend employed in the tests was a fully formulated SAE Grade 30 mineral lubricating oil composition. The composition of the lubricant and the test results are set forth in the table below:

TABLE IV

| Composition | Wt. % |
| --- | --- |
| Dispersant of Example 24 | 7.7 |
| 0.15% zinc as zinc dialkyldithiophosphate | 1.35 |
| 0.23% calcium as overbased calcium sulfonate | 1.47 |
| Dinonyldiphenylamine | 0.25 |
| Methacrylate ester | 0.05 |
| Silicone antifoamant | 150 ppm |
| Mineral oil | 89.18 |

SEQUENCE VC TEST RESULTS

| | |
| --- | --- |
| Sludge (Average) | 9.6 |
| Varnish (Average) | 8.3 |
| Piston Skirt Varnish | 8.3 |

The foregoing test results indicate outstanding engine cleanliness for the lubricating oil composition of the invention in the Ford Sequence VC Engine Test.

We claim:

1. A quaternary ammonium salt of an esterlactone represented by the formula:

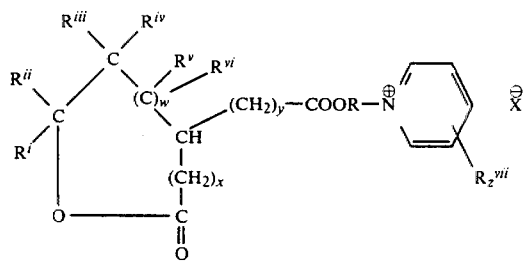

in which w represents 0 or 1, x and y alternately represent 0 and 1, z has value from 0 to 2, $R^i$, $R^{ii}$, $R^{iii}$, $R^{iv}$, $R^v$ and $R^{vi}$, represent hydrogen, a methyl radical or a hydrocarbyl radical of 50–200 carbon atoms only one of which is said hydrocarbyl radical, R is a divalent hydrocarbon radical having from 2–10 carbon atoms, $R^{vii}$ is hydrogen or a hydrocarbyl radical having from 1 to 3 carbon atoms, and X is an anion selected from the group consisting of halide, sulfate, carbonate, sulfite, borate, carboxylate, and phosphate.

2. A quaternary ammonium salt according to claim 1 in which said anion is the chloride ion.

3. A quaternary ammonium salt according to claim 1 in which said anion is the sulfate ion.

4. A quaternary ammonium salt according to claim 1 in which said anion is a borate anion.

5. A quaternary ammonium salt according to claim 1 in which said hydrocarbyl radical has from 75 to 150 carbon atoms.

6. A quaternary ammonium salt according to claim 1 in which R is a divalent hydrocarbon radical having from 2 to 6 carbon atoms and $R^{vii}$ is hydrogen or a methyl radical.

7. A quaternary ammonium salt of an ester-gamma-lactone represented by the formula:

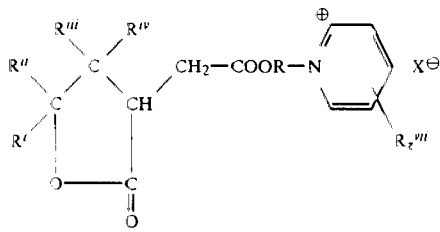

in which $R^i$ and $R^{iii}$ alternately represent hydrogen and a hydrocarbyl radical having from 50 to 200 carbon atoms, $R^{ii}$, and $R^{iv}$ represent hydrogen or a methyl radical, R is a divalent hydrocarbon radical having from 2 to 6 carbon atoms, X is an anion selected from the group consisting of chloride, bromide, sulfate and borate ions, $R^{vii}$ is hydrogen or an aliphatic hydrocarbon radical having from 1 to 3 carbon atoms and z has a value from 0 to 2.

8. A quaternary ammonium salt of an ester-gamma-lactone represented by the formula:

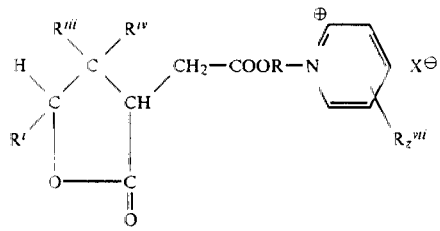

in which $R^i$ represents a hydrocarbyl radical having from 50 to 200 carbon atoms, $R^{iii}$ and $R^{iv}$ represent hydrogen or a methyl radical, R is a divalent hydrocarbon radical having 2 carbon atoms, X is an anion selected from the group consisting of chloride and bromide ions, $R^{vii}$ is hydrogen or an aliphatic hydrocarbon radical having from 1 to 3 carbon atoms and z has a value from 0 to 2.

9. A quaternary ammonium salt of an ester-gamma lactone represented by the formula:

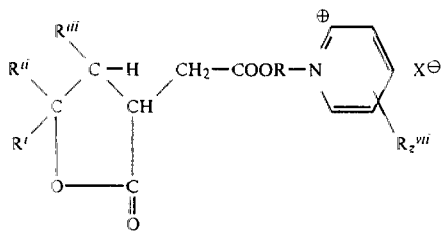

in which $R^{iii}$ represents a hydrocarbyl radical having from 50 to 200 carbon atoms, $R^i$ and $R^{ii}$ represent hydrogen or a methyl radical, R is a divalent hydrocarbon radical having 2 carbon atoms, X is an anion selected from the group consisting of chloride and bromide ions, $R^{vii}$ is hydrogen or an aliphatic hydrocarbon radical having from 1 to 3 carbon atoms and z has a value from 0 to 2.

10. A quaternary ammonium salt according to claim 7 in which said hydrocarbyl radical has from 75 to 150 carbon atoms.

11. A quaternary ammonium salt according to claim 7 in which said hydrocarbyl radical is a polyisobutenyl radical.

12. A quaternary ammonium salt according to claim 7 in which $R^{vii}$ is hydrogen or a methyl radical.

13. A quaternary ammonium salt according to claim 7 in which said anion is the chloride ion.

14. A quaternary ammonium salt according to claim 7 in which said anion is a borate ion.

15. A lubricating oil composition comprising a major portion of a mineral lubricating oil and a minor dispersant amount of a quaternary ammonium salt of an ester-lactone represented by the formula:

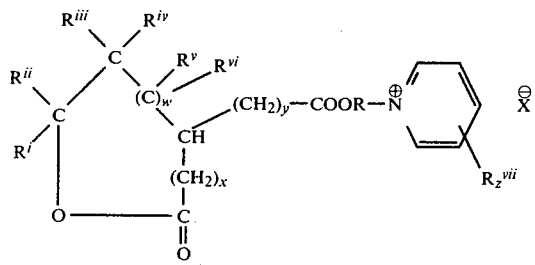

in which w represents 0 or 1, x and y alternately represent 0 and 1, z has value from 0 to 2, $R^i$, $R^{ii}$, $R^{iii}$, $R^{iv}$, $R^v$ and $R^{vi}$, represent hydrogen, a methyl radical, or a hydrocarbyl radical of 50–200 carbon atoms only one of which is said hydrocarbyl radical, R is a divalent hydrocarbon radical having from 2–10 carbon atoms, $R^{vii}$ is hydrogen or a hydrocarbyl radical, having from 1 to 3 carbon atoms and X is an anion selected from the group consisting of halide, sulfate, carbonate, sulfite, borate, carboxylate, and phosphate anions.

16. A lubricating oil composition according to claim 15 having a quaternary ammonium salt in which R is a divalent hydrocarbon radical having from 2 to 6 carbon atoms and $R^{vii}$ is hydrogen or a methyl radical.

17. A lubricating oil composition according to claim 15 having a quaternary ammonium salt in which said hydrocarbyl radical has from 75 to 150 carbon atoms.

18. A lubricating oil composition according to claim 15 in which said anion is the chloride ion.

19. A lubricating oil composition according to claim 15 in which said anion is the borate ion.

20. A lubricating oil composition according to claim 15 in which said anion is the sulfate ion.

21. A lubricating oil composition comprising a major portion of a mineral lubricating oil and a minor dispersant amount of a quaternary ammonium salt of an ester-gamma-lactone represented by the formula:

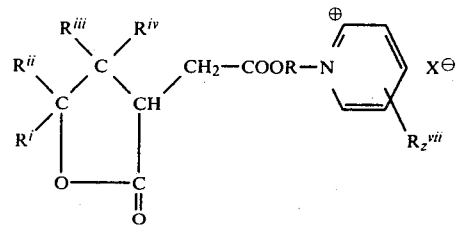

in which $R^i$ and $R^{iii}$ alternately represent hydrogen and a hydrocarbyl radical having from 50 to 200 carbon atoms, $R^{ii}$, and $R^{iv}$ represent hydrogen or a methyl radical, R is a divalent hydrocarbon radical having from 2 to 6 carbon atoms, X is an anion selected from the group consisting of chloride, bromide, sulfate and borate ions, $R^{vii}$ is hydrogen or an aliphatic hydrocarbon radical having from 1 to 3 carbon atoms and z has a value from 0 to 2.

22. A lubricating oil composition according to claim 21 in which said hydrocarbyl radical has from 75 to 150 carbon atoms.

23. A lubricating oil composition according to claim 21 in which said hydrocarbyl radical is a polyisobutenyl radical.

24. A lubricating oil composition according to claim 21 having a quaternary ammonium salt in which said anion is the cloride ion.

25. A lubricating oil composition according to claim 21 having a quaternary ammonium salt in which said anion is the borate ion.

26. A lubricating oil composition according to claim 21 having a quaternary ammonium salt in which said anion is the sulfate ion.

27. A lubricating oil composition according to claim 21 in which said salt is represented by the formula:

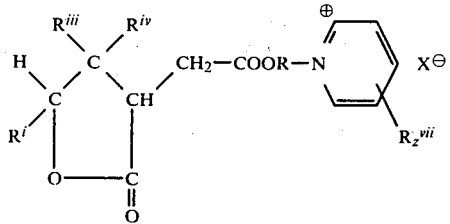

in which $R^i$ represents a hydrocarbyl radical having from 50 to 200 carbon atoms, $R^{iii}$ and $R^{iv}$ represent hydrogen or a methyl radical, R is a divalent hydrocarbon radical having 2 carbon atoms, X is an anion selected from the group consisting of chloride and bromide ions, $R^{vii}$ is hydrogen or an aliphatic hydrocarbon radical having from 1 to 3 carbon atoms and z has a value from 0 to 2.

28. A lubricating oil composition according to claim 21 in which said salt is represented by the formula:

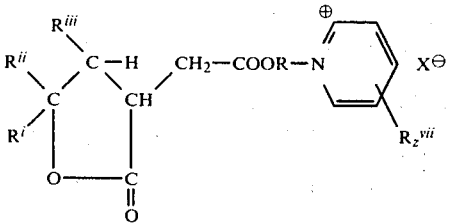

in which $R^{iii}$ represents a hydrocarbyl radical having from 50 to 200 carbon atoms, $R^i$ and $R^{ii}$ represent hydrogen or a methyl radical, R is a divalent hydrocarbon radical having 2 carbon atoms, X is an anion selected from the group consisting of chloride and bromide ions, $R^{vii}$ is hydrogen or an aliphatic hydrocarbon radical having from 1 to 3 carbon atoms and z has a value from 0 to 2.

* * * * *